United States Patent
Bzdusek

(10) Patent No.: US 8,663,084 B2
(45) Date of Patent: Mar. 4, 2014

(54) METHOD AND APPARATUS FOR INTENSITY MODULATED ARC THERAPY SEQUENCING AND OPTIMIZATION

(75) Inventor: Karl Antonin Bzdusek, Fitchburg, WI (US)

(73) Assignee: Koninklijke Philips N.V., Eindhoven (NL)

( * ) Notice: Subject to any disclaimer, the term of this patent is extended or adjusted under 35 U.S.C. 154(b) by 798 days.

(21) Appl. No.: 12/682,597

(22) PCT Filed: Oct. 2, 2008

(86) PCT No.: PCT/IB2008/054022
§ 371 (c)(1),
(2), (4) Date: Apr. 12, 2010

(87) PCT Pub. No.: WO2009/050615
PCT Pub. Date: Apr. 23, 2009

(65) Prior Publication Data
US 2010/0219356 A1    Sep. 2, 2010

Related U.S. Application Data

(60) Provisional application No. 60/980,228, filed on Oct. 16, 2007, provisional application No. 61/012,480, filed on Dec. 10, 2007.

(51) Int. Cl.
*A61N 5/00* (2006.01)

(52) U.S. Cl.
USPC .............. 600/1; 378/65; 250/492.1; 128/897; 128/898

(58) Field of Classification Search
USPC ....... 600/1; 250/492.1; 378/65; 128/897, 898
See application file for complete search history.

(56) References Cited

U.S. PATENT DOCUMENTS

| | | | |
|---|---|---|---|
| 5,818,902 A | 10/1998 | Yu | |
| 6,393,096 B1 * | 5/2002 | Carol et al. | 378/65 |
| 6,477,229 B1 * | 11/2002 | Grosser | 378/65 |
| 6,907,105 B2 | 6/2005 | Otto | |
| 2004/0071261 A1 | 4/2004 | Earl et al. | |
| 2006/0256915 A1 | 11/2006 | Otto et al. | |
| 2008/0298550 A1 * | 12/2008 | Otto | 378/65 |
| 2009/0213991 A1 * | 8/2009 | Brown et al. | 378/65 |
| 2009/0225942 A1 * | 9/2009 | Shepard et al. | 378/65 |

FOREIGN PATENT DOCUMENTS

WO    2007012185 A1    2/2007

OTHER PUBLICATIONS

Gladwish, A., et al.; Segmentation and leaf sequencing for intensity modulated arc therapy; 2007; Med. Phys.; 34(5) 1779-1788.
Shepard, D.M., et al.; An arc-sequencing algorithm for intensity modulated arc therapy; 2007; Med. Phys.; 34(2) 464-470.
Yu, C. X.; Modulated Radiotherapy-Current Status and New Developments; 2006; Business Briefing U.S. Oncology Review; pp. 1-4.
Yu, C. X.; Intensity-modulated arc therapy with dynamic multileaf collimation: an alternative to tomotherapy; 1995; Phys. Med. Biol.; 40:1435-1449.

* cited by examiner

*Primary Examiner* — Christine Matthews
*Assistant Examiner* — Sunita Reddy

(57) ABSTRACT

A treatment planner (102) generates fluence maps (140) indicative of a desired fluence distribution at various locations (304, 312) along a treatment arc (302). A converter (142) converts the fluence distributions (140) to treatment device settings (144). The settings (144) may include multiple segments. A segment distributor (146) distributes the settings to locations in the vicinity of their original positions.

19 Claims, 4 Drawing Sheets

METHOD AND APPARATUS FOR INTENSITY MODULATED ARC THERAPY SEQUENCING AND OPTIMIZATION

CROSS REFERENCE TO RELATED APPLICATIONS

This application claims the benefit of U.S. provisional application Ser. No. 60/980,228 filed Oct. 16, 2007 and Ser. No. 61/012,480 filed Dec. 10, 2007, both of which are incorporated herein by reference.

DESCRIPTION

The present application relates to radiation treatment. While it finds particular application to radiation treatment in medical oncology, it also relates to other medical and non-medical applications in which it is necessary to apply a radiation dose to an object undergoing treatment.

Intensity Modulated Radiation Therapy (IMRT) is a treatment technique that was developed in the 1990's and has been in clinical use worldwide since about 2000. IMRT has the advantage of producing treatment plans in which organs at risk receive much lower doses compared with traditional treatment techniques. Clinical IMRT treatments have been using static beams (where the gantry does not move during treatment) exclusively; only the multi-leaf collimator (MLC) moves.

Traditional IMRT treatments are delivered at predetermined angles around a patient. At each angle there is a series of segments or MLC aperture shapes. While the treatment machine is moving between angles or segments, the beam is turned off. This "dead time" extends treatment times.

Intensity Modulated Arc Therapy (IMAT) uses arc beams instead of static beams. In traditional IMRT as well as in IMAT treatments, the amount of MLC leaf travel partially determines how long a treatment will take. IMAT has the advantage over traditional IMRT that it can produce treatments where the organs at risk receive even less dose while the tumor still receives the prescribed dose in a much shorter delivery time. By using a continuous IMAT arc, the beam is always on thus eliminating the dead time.

Another aspect of IMAT techniques is in the streamlining of the treatment planning process. In general, it is desirable to produce a treatment plan that maximizes the therapeutic dose applied to tumors or other lesions while minimizing the damage to surrounding tissues. To achieve accurate dose distributions for some cases, a large number of beam angles may be required. Increasing the number of such angles generally increases the workload and computational complexity of the treatment planning process. This in turn tends to increase the treatment planning time or conversely, requires the use of relatively more powerful computers. In IMAT planning, the user may only have to specify the arc parameters and for many cases, default values will be appropriate.

Other things being equal, it is desirable to reduce the time required to apply a desired treatment to the patient while still delivering a treatment that approximates the prescribed dose. Similarly, it is desirable to reduce the computational complexity of the treatment planning process.

Aspects of the present application address these matters and others. According to a first aspect, a method includes, for an intensity modulated arc therapy treatment plan that includes first and second segments at a first angular location along an arc, determining a desired distribution of the first and second segments along the arc with each segment at a unique angular position. The method also includes distributing the first and second segments according to the determined distribution.

According to another aspect, an apparatus includes means for determining, for an intensity modulated arc therapy treatment plan that includes first and second segments at a location along an arc, desired positions of the first and second segments along the arc. The apparatus also includes means for positioning the first and second segments according to the desired positions.

According to another aspect, a computer readable storage medium contains instructions which, when executed by a computer processor, cause the processor to carry out a method. The method includes, in connection with a radiation treatment plan that includes first and second segments located at a first beam position along a treatment delivery arc, repositioning the first segment to a first sub-position and repositioning the second segment to a second sub-position.

According to another aspect, a computer readable storage medium contains instructions which, when executed by a processor, cause the processor to carry out a method. The method includes, in connection with an intensity modulated arc therapy treatment plan that includes first and second segments located at a first beam position along a treatment arc, distributing the first and second segments along the arc in the vicinity of the first location.

The present invention is illustrated by way of example and not limitation in the figures of the accompanying drawings, in which like references indicate similar elements and in which.

Figure 3A:
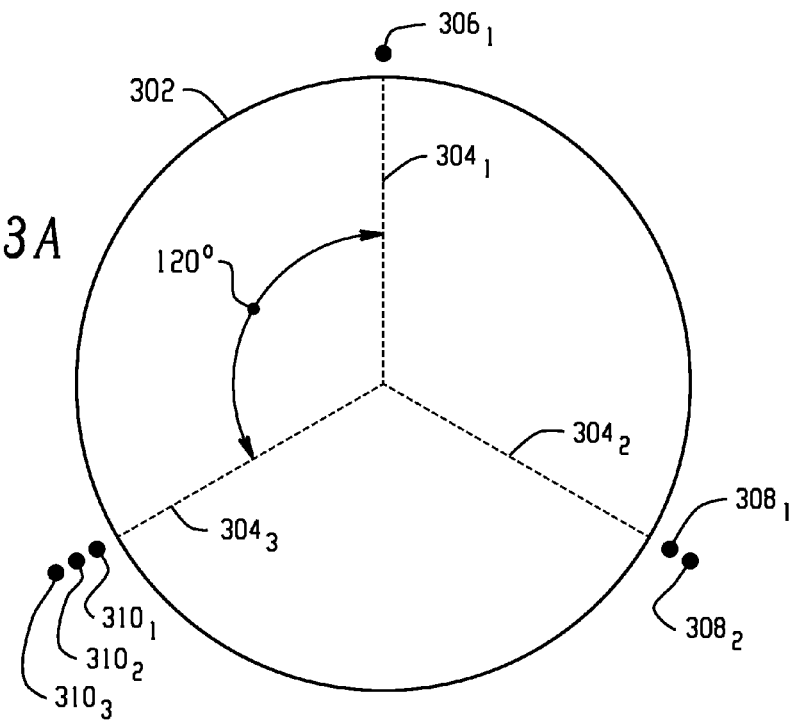
Figure 3B:
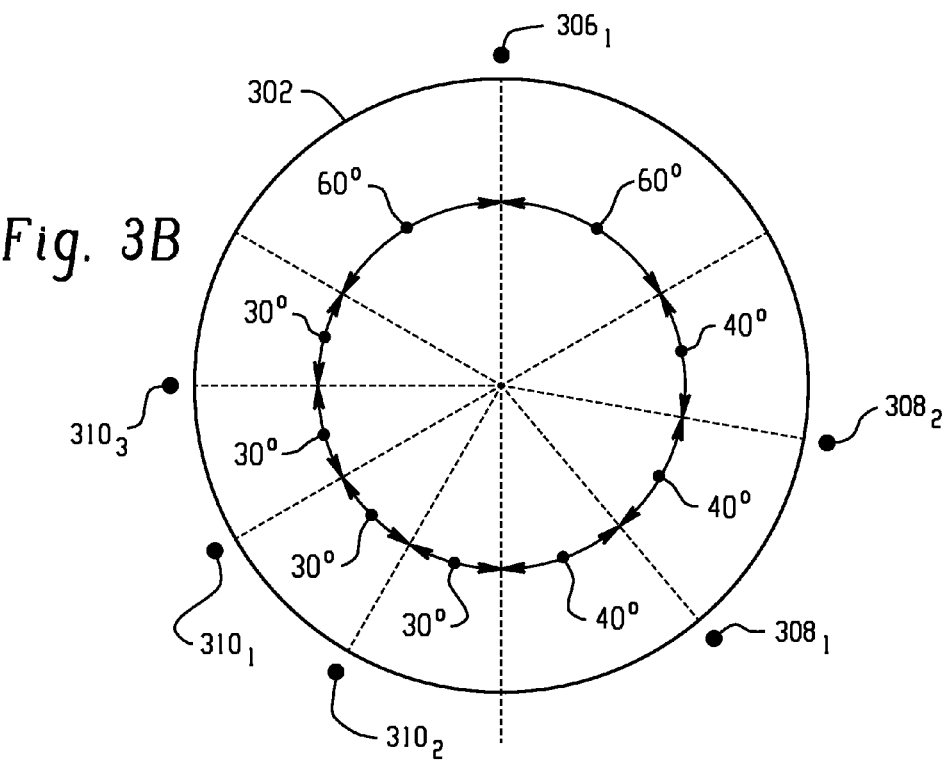
Figure 3C:
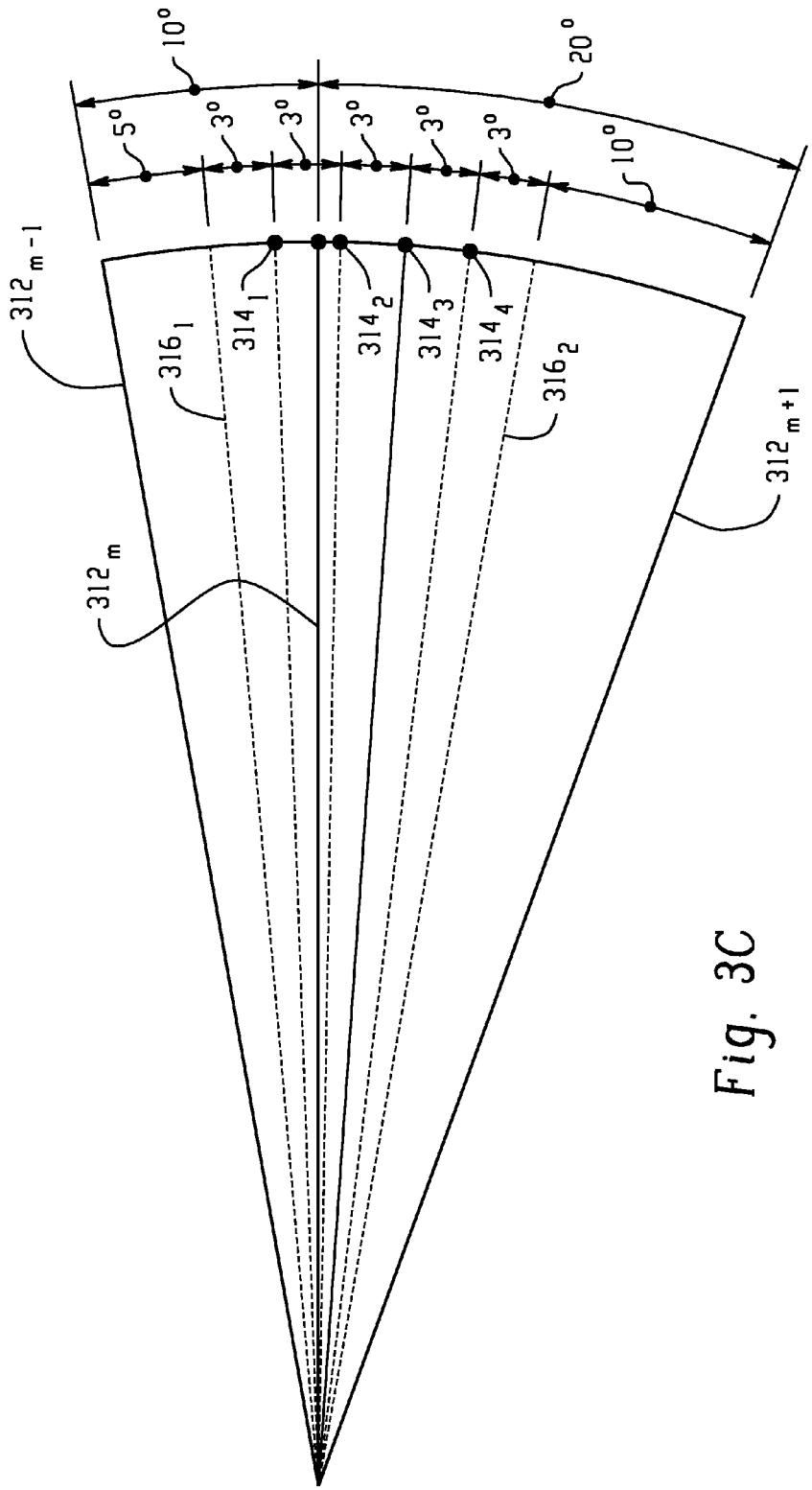

FIGS. 3A, 3B, and 3C depict beam positions, segments, and re-positioned segments.

Figure 1:
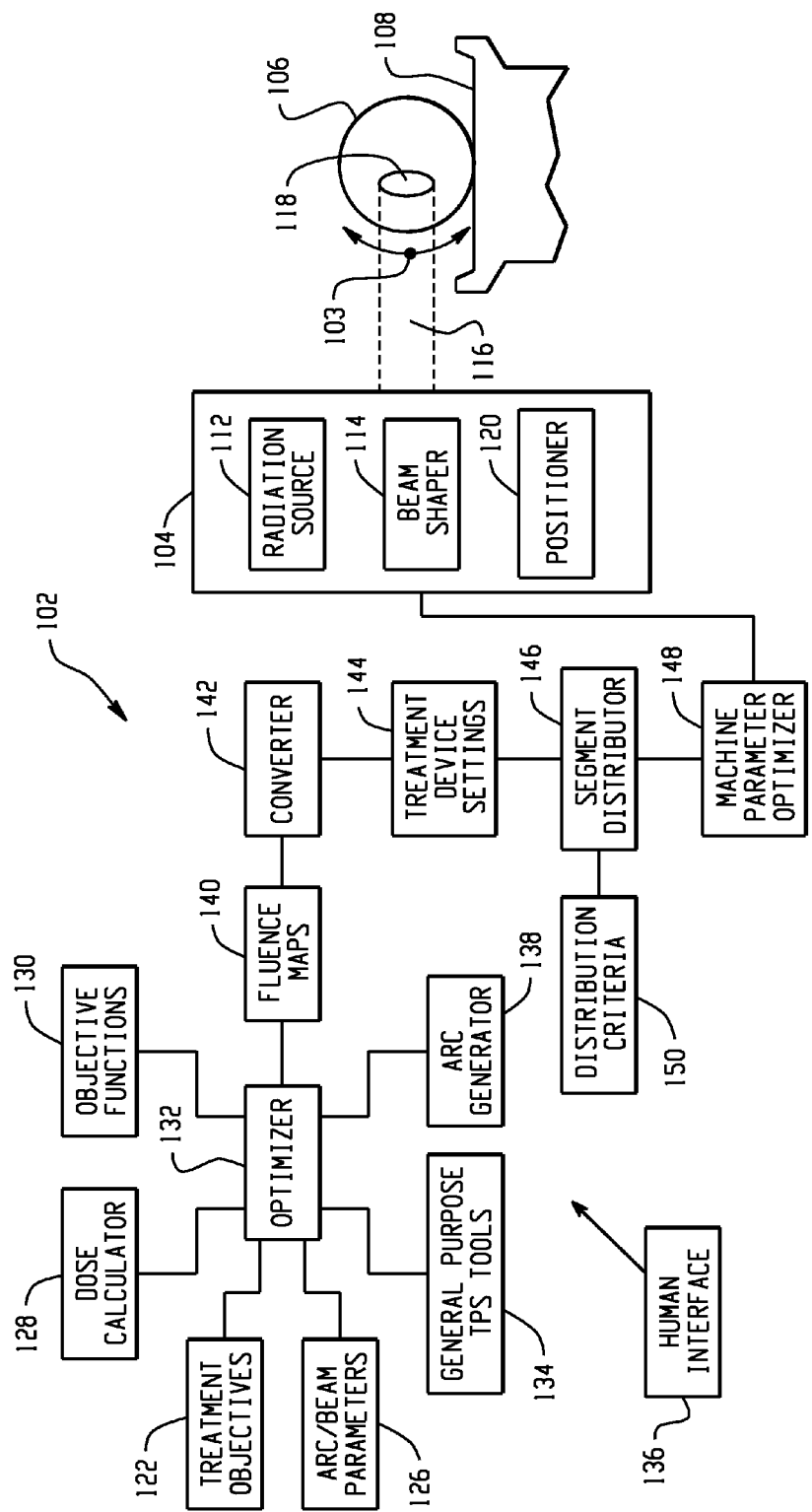
FIG. 1 depicts a treatment planning and delivery system.

Turning now to FIG. 1, a radiation treatment planner 102 develops a treatment plan for delivery by a radiation treatment delivery system 104.

As illustrated, the delivery system 104 includes a radiation source 112, a beam shaper 114, and a positioner 120. The radiation source 112 may include a linear accelerator, a radioactive material, a particle radiation source (e.g., a proton source), or other source of ionizing radiation.

The beam shaper 114 shapes the radiation from the radiation source 112 to produce a spatially varying radiation beam 116 that is applied to a target 118 of an object 106. Thus, for example, the shape of the beam may be adjusted to conform generally to the shape of the target 118 when viewed along the direction of the beam 116 (i.e., along a beam's eye view). The beam shaper 114 may also be operated to adjust the relative spatial intensity of the beam 116 so that relatively higher (or lower) radiation doses are applied to different regions of the target 118.

In one implementation, the beam shaper 114 includes a multi leaf collimator (MLC). MLCs typically include a plurality of moveable radiation attenuative leaves interposed between the radiation source 112 and the object 106. The leaves thus define an aperture through which the radiation is delivered. Typically, MLCs also include an adjustable collimator angle setting that defines a rotational position of the MLC about an axis that is generally parallel to the axis of the beam 116. Thus, the MLC aperture and collimator angle settings serve to adjust the time-varying characteristics of the radiation beam 116.

A positioner 120 varies the relative positions of the beam 116 and the object 106 so that the radiation is applied from a number of different directions or beam positions. Depending on the configuration of the delivery system 104, the positioner 120 settings may address matters such as patient couch 108 angle and/or spatial position, the angular position of the radiation source 112 and beam shaper 114 relative to the object 106, and the like.

In the case of an intensity modulated arc therapy (IMAT) system, the beam 116 traverses one or more arcs or trajectories 103 relative to the target 118. The angular rate of motion of beam 116 can vary around the arc 103. Radiation is ordinarily applied temporally concurrently with the relative movement of the beam 116, with the beam shaper 114 settings being varied along with the motion of the beam 116. The beam 116 will likely have a variable dose rate between different arc segments and the beam 116 need not be continuously applied, and may for example be turned off at those positions in which the beam 116 would otherwise adversely affect a risk organ.

The treatment planner 102 plans an IMAT treatment to be applied by the treatment device 104. More particularly, the treatment planner 102 seeks to develop a treatment plan that optimally satisfies treatment objective(s) 122 such as one or more of a minimum dose to be applied to the target 118, a maximum radiation dose to be applied outside the target 118 (e.g., to a risk organ or to otherwise healthy tissue), minimum and maximum dose volume objectives, dose uniformity objectives, and the like.

The arc/beam parameters 126 describe parameter(s) such as one or more of desired starting and ending angle(s) for the beam trajectory, couch angles, and the like that are used by the treatment planner 102 in developing the treatment plan. Alternately, one or more of the arc/beam parameters 126 may be treated as variables that are optimized by the treatment planner 102 or optimizer 132.

As illustrated, the treatment planner 102 includes a dose calculator 128, one or more objective functions 130, an optimizer 132, and general purpose treatment planning software (TPS) tools 134. Suitable dose calculator 128 and TPS tools 134 are currently available on many currently available TPS systems. Most TPS systems also have an IMRT optimizer and objective function(s) that can be suitably modified and/or reused for use as the optimizer 132 and the objective functions 130.

The treatment planning system also includes a human interface 136 such as a computer-implemented graphical user interface (GUI) that guides the user through the arc generation and optimization process. The human interface 136 may also allow the user to define the arc parameters manually for a number of combinations of parameters that may be computed in one sequence.

The treatment planner 102 may also include an arc generator 138 that determines optimal arc/beam parameters 126, particularly in situations where such parameters are difficult to define by the user.

The optimizer 132 produces fluence maps 140 for various beam positions (which beam positions are sometimes referred to as control points) along one or more of the arcs. In a typical IMAT treatment plan, the beam positions are initially spaced at intervals of about every ten (10) to twenty (20) degrees, although greater or lesser numbers of beam positions are contemplated, as are unequal spacings. In general, increasing the number of beam positions gives the optimizer 132 more degrees of freedom and produces a more accurate dose distribution. However, increasing the number of beam positions also tends to increase the complexity of the necessary calculations, and thus the time necessary to generate the treatment plan. Therefore increasing the number of beams has a point of diminishing returns.

A converter 142 converts the fluence maps 140 into a treatment plan that include treatment device settings 144 that approximate or otherwise produce the desired fluence maps. More particularly, for each beam position along the arc(s), the converter generates beam shaper 114 settings (e.g., aperture settings and collimator angles in the case of an MLC) that produce the desired fluence distributions. Depending on the complexity of the desired fluence distribution, the beam positions may include a number of segments. Care may be taken to limit the number of treatment device settings 144 to ensure that the remainder of the optimization is not unnecessarily overburdened. Each segment includes a different beam shaper 114 setting. Again to the example of an MLC, the segments may include different aperture and/or collimator angle settings.

As will be appreciated, implementing multiple segments at a given beam position would ordinarily increase the time needed to deliver an IMAT treatment because multiple arc rotations would be required. A relatively large number of segments at a given beam position also indicates a relatively high degree of spatial complexity at the beam position. One approach to this problem is to establish additional beam positions in the vicinity of the original beam position and continue the optimization process so as to reduce the number of segments at the beam position. However, doing so tends to increase the complexity of the planning process.

Alternately or additionally, then, a segment distributor 146 distributes the various segments along the arc. More particularly, for each beam position, the segment distributor 146 distributes the segment(s) of the beam position to sub-position(s) in the vicinity of the beam position. The sub-positions are preferably selected so as that the dose distribution imparted by the distributed segments approximates that of the original segments.

More particularly, the location of the sub-positions, the order in which the segments are distributed along the arc, and other relevant aspects of the distribution are established according to distribution criteria 150. For example, the order in which the segments are located among the sub-positions may be selected to minimize the required beam shaper 114 motion. In the case of an MLC, for example, the order may be selected to minimize the motion and/or velocity or motion of the MLC leaves. As another example, the locations of the sub-positions may be selected based on the number of segments to be distributed and the locations of adjacent beam positions. Still further, the sub-positions may be centered between the locations that represent the midpoints between the beam position for which the segments are being distributed and the first order neighbors of the beam position. Depending on factors such as the positions of the first order neighbors and the number of segments to be distributed, the sub-positions may or may not be symmetrical with respect to the beam position. Example segment distributions and sub-positions will be described in further detail below.

A machine parameter optimizer 148 uses direct machine parameter optimization techniques to further optimize the distributed segments, for example to minimize leaf motion and to avoid machine restrictions. If the optimizer 148 determines that the requested objectives can not be met, additional segments can be intelligently inserted based on segments rejected during the conversion process 142.

Figure 2:
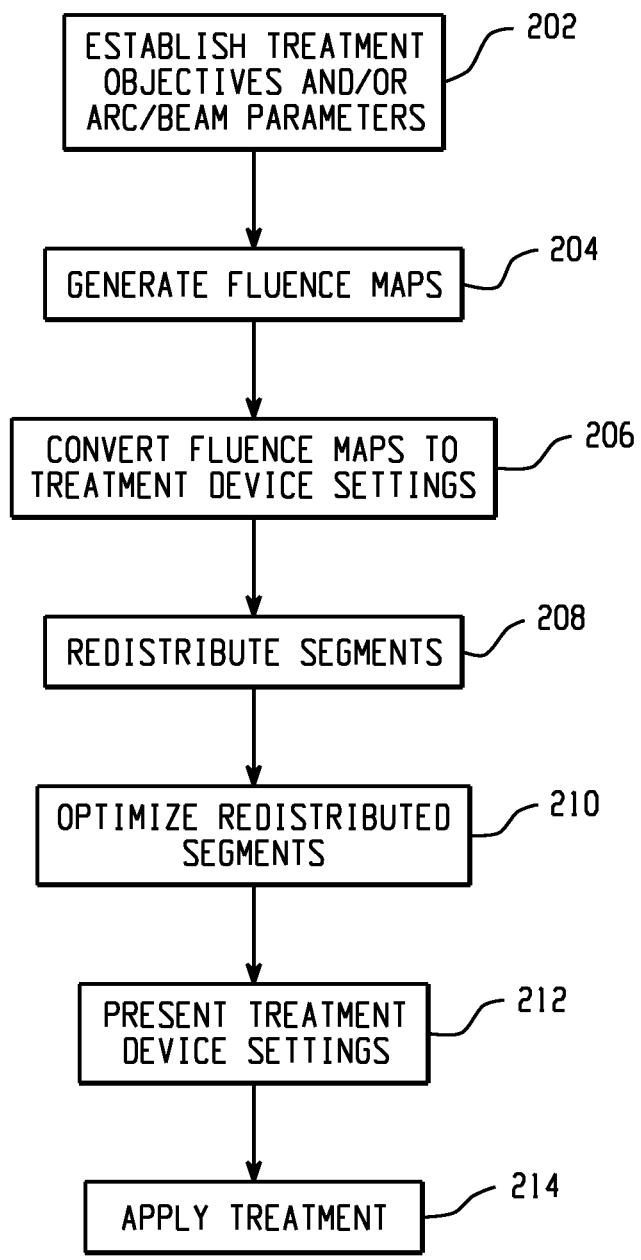
FIG. 2 depicts a method.

Operation will now be described with reference to FIGS. 2 and 3.

Treatment objectives are established at 202.

Fluence maps are generated at 204. For simplicity of illustration, and with reference to FIG. 3A, it will be assumed that the treatment plan includes a 360° degree circular trajectory or arc 302 and that fluence maps are generated at three (3)

beam positions $304_1, 304_2, 304_3$ that are equally spaced along the trajectory (i.e., at 120° intervals).

The fluence maps are converted to treatment device settings at 206. Again for the purposes of explanation, it will be assumed that one (1) segment $306_1$ is required at the first beam position $304_1$, two (2) segments $308_{1,2}$ are required at the second beam position $304_2$, and three (3) segments $310_{1,2,3}$ are required at the third beam position $304_3$.

The segments 306, 308, 310 are redistributed at 208. In one implementation, the angular distance between the sub-positions is calculated as follows:

$$\theta_S = \frac{\theta_{m-1} - \theta_{m+1}}{(N+1)} \quad \text{Equation 1}$$

where $\theta_s$ is the distance between the sub-positions for beam position m, $\theta_{m-1}$ is the beam position for a first order neighbor on a first side of beam position m, $\theta_{m+1}$ is the beam position for a first order neighbor on a second side of beam position m, and N is the number of segments for beam position m. On the first side, the outermost beam sub-position is offset from the location midway between the beam position m−1 and beam position m by the distance $\theta_s$. On the second side, the outermost beam sub-position is likewise offset from the location midway between the beam position m+1 and beam position m by the distance $\theta_s$.

Such a distribution of the beam positions and segments of FIG. 3A is shown at FIG. 3B. Thus, the position of beam segment $306_1$ is unchanged, beam segments $308_1$ and $308_2$ are spaced apart by an angular distance of forty degrees (40°), and beam segments $310_1, 310_2, 310_3$ are spaced apart by an angular distance of thirty degrees) (30°). Note that the order in which the segments are distributed along the arc 302 is selected based on a desired ordering criteria.

FIG. 3C depicts the redistribution of N=4 segments $314_{1-4}$ with respect to a beam position $312_m$. As illustrated, the treatment plan is such that the distances between beam position $312_m$ and the neighboring beam positions are unequal: ten degrees) (10°) in the case of beam position $312_{m-1}$ and twenty degrees)(20°) in the case of beam position $312_{m+1}$. The sub-positions are spaced by a distance of three degrees (3°). As will also be appreciated, the sub-positions are centered relative to the beam position mid-points $316_1, 316_2$ on the respective first and second sides of beam position $312_m$.

One advantage of such an arrangement is that the redistribution tends to mirror the spatial complexity of the treatment plan. Those regions of the arc that require a relatively complex fluence distribution receive a relatively larger number of sub-positions. Moreover, the distribution of segments from adjacent beam positions does not overlap.

The redistributed segments are optimized at step 210 to produce treatment device settings.

At 212, the treatment device settings are presented to the treatment device 104.

The treatment is applied to the subject at 214.

Variations are contemplated. For example, the spacing between the redistributed segments of a given beam location may be unequal. Moreover, the various segments of a beam location may be positioned along a range of sub-positions that are relatively nearer to, or farther from, the beam location than as described in Equation 1. In the former case, the applied treatment will generally tend to more closely approximate the desired treatment. In the latter case, the treatment delivery is relatively less likely to be constrained by the motion characteristics of the beam shaper 114. Moreover, the spacing between the various sub-positions may also be determined as a function of beam locations that are second (or higher) order neighbors of the beam location for which the segments are being redistributed.

The order in which the segments are distributed along may also be varied based on criteria other than beam shaper 114 motion. For example, segments may be distributed so as to provide a dose distribution that most closely approximates the desired dose distribution.

Segments may also be filtered if for one or more reasons their contribution to the treatment plan does not meet certain criteria. For example, segments that have a monitor unit setting below a certain threshold may cause the treatment dose rate to be reduced and not provide much contribution to the treatment plan. Another example could be two adjacent segments with dramatically different beam shaper 114 settings. It might be inefficient to deliver this arc segment and, unless it can be redistributed, filtering might be beneficial.

Still further, the planning process may also include multiple trials with different numbers of arcs and/or arc parameters. In such a case, the results of the various trials may be presented to the user in a comparison GUI that would present image set/dose distribution windows, device volume histogram (DVH) curves, and/or other information that would allow the user to evaluate the various treatment plans.

It will be appreciated that variations of the techniques above may be implemented via varying combinations of hardware and/or computer software or firmware. In the case of software, firmware, or the like, computer readable instructions may be stored on a computer readable storage medium. When executed by a computer processor, the instructions cause the processor to carry out the described techniques. The instructions may also be located remotely and accessed as required, for example by downloading them via the internet.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A method comprising:

for an intensity modulated arc therapy treatment plan that includes first and second segments at a same first location along an arc, determining a first desired distribution of the first segment along the arc and a second desired distribution of the second segment along the arc, wherein the first and second desired distributions correspond to locations, of a source moving along the arc, that are different from the first location and that are different from each other, and the intensity modulated arc therapy treatment plan includes a third segment at the first location;

determining a desired distribution of the third segment, which includes distributing the third segment according to a determined desired distribution of the third segment in which a spacing between the first and second segments is equal to a spacing between the second and third segments according to the relation:

$$\theta_S = \frac{\theta_{m-1} - \theta_{m+1}}{(N+1)},$$

wherein $\theta_s$ is a distance between sub-positions for a beam position m, $\theta_{m-1}$ is a beam position for a first order neighbor on a first side of beam position m, $\theta_{m+1}$ is a beam position for a first order neighbor on a second side of beam position m, and N is a number of segments for beam position, and;

distributing, via a computer processor, the first and second segments according to the determined first and second desired distributions.

2. The method of claim 1 wherein the determined first and second desired distributions include an order.

3. The method of claim 1 including positioning the first segment at a first position along the arc and the second segment at a second position along the arc.

4. The method of claim 1 wherein the intensity modulated arc therapy treatment plan includes second and third locations along the arc, the second and third locations each include a segment, the distributed first segment of the first location is disposed between the first and second locations and a first distance from the midpoint of the first and second locations, the distributed second segment is disposed a second distance from the midpoint of the first and third locations, and the first and second distances are equal.

5. The method of claim 1 wherein determining a desired distribution of the first and second segments includes determining an order of the segments along the arc that minimizes a motion of a beam shaper.

6. The method of claim 1 including:
determining a desired fluence distribution at the first location;
converting the fluence distribution to treatment device settings that produce the desired fluence distribution, wherein the settings include the first and second segments.

7. The method of claim 1 including optimizing the distributed segments according to a direct machine parameter optimization technique.

8. An apparatus comprising:
means for determining, for an intensity modulated arc therapy treatment plan that includes first and second segments at a same location along an arc, a first position of the first segment and a second position of the second segment along the arc, wherein the first and second positions are different from the same location and each other,
means for determining first and second sub-positions as a function of a distance between the first and second positions, wherein the second position is a first order neighbor of the first position on a first side of a third position and the first position is a first order neighbor of the second beam position on a second side of the third position, and;
means for positioning the first and second segments according to the first and second positions.

9. The apparatus of claim 8 including:
an optimizer that determines a desired fluence distribution at the same location;
a converter that converts the fluence distribution to treatment device settings that include the first and second segments.

10. The apparatus of claim 8 including a radiation treatment device.

11. A computer readable storage device that contains instructions which, when executed by a computer processor, cause the processor to carry out a method that includes, in connection with a radiation treatment plan that includes first and second segments located at a same first beam position along a treatment delivery arc and a second beam position that is a first order neighbor of the first beam position on a first side of the first beam position and a third beam position that is a first order neighbor of the first beam position on a second side of the first beam position:
repositioning the first segment to a first sub-position, which is different from the same first beam position;
repositioning the second segment to a second sub-position, which is different from the same first beam position and the first sub-position; and
determining the first and second sub-positions as a function of the distance between the second and third beam positions.

12. The computer readable storage device of claim 11 wherein the radiation treatment plan includes third and fourth segments located at a same second beam position along the treatment delivery arc and the method includes:
repositioning the third segment to a third sub-position, which is different from the same second beam position;
repositioning the fourth segment to a fourth sub-position, which is different from the same second beam position and the third sub-position.

13. The computer readable storage device of claim 11 wherein the method includes further determining the first and second sub-positions as a function of the number of segments located at the first beam position.

14. The computer readable storage device of claim 11 wherein the radiation treatment plan includes a third segment located at the first beam position and the method includes:
repositioning the third segment to a third sub-position;
selecting relative locations of the first and second sub-positions so as to minimize a motion of a treatment delivery device.

15. The computer readable storage device of claim 11 wherein the method includes generating the radiation treatment plan.

16. A computer readable storage device containing instructions which, when executed by a processor, cause the processor to carry out a method that includes, in connection with an intensity modulated arc therapy treatment plan that includes first and second segments located at a same first beam position along a treatment arc, distributing the first and second segments along the arc at different positions, which are in a vicinity of but not the same as the same first beam position, wherein the first beam position is located between second and third beam positions that are first order neighbors of the first beam position, the first beam position includes a plurality of segments, and distributing each of the plurality of segments so that the distributed segments are located nearer the first beam position than to the second beam position or the third beam position.

17. The computer readable storage device of claim 16 wherein the radiation treatment plan includes the first and second segments located at the first beam position and the method includes repositioning each of the plurality of segments.

18. The computer readable storage device of claim 16 wherein the method includes optimizing the distributed segments.

19. The computer readable storage device of claim 16 wherein the method includes presenting information indicative of the distributed segments to a treatment device.

* * * * *